US006652445B1

United States Patent
Woo

(10) Patent No.: US 6,652,445 B1
(45) Date of Patent: *Nov. 25, 2003

(54) TREATMENT OF AFFLICTIONS AILMENTS AND DISEASES

(76) Inventor: Gilson Woo, 19708 Balan Rd., Rowland Heights, CA (US) 91748

( * ) Notice: Subject to any disclaimer, the term of this patent is extended or adjusted under 35 U.S.C. 154(b) by 0 days.

This patent is subject to a terminal disclaimer.

(21) Appl. No.: 09/722,239

(22) Filed: Apr. 28, 2001

Related U.S. Application Data

(63) Continuation-in-part of application No. 08/939,429, filed on Sep. 26, 1997, now abandoned.

(51) Int. Cl.⁷ .................................................. A61N 1/00
(52) U.S. Cl. ................................................................ 600/15
(58) Field of Search ........................ 600/13–15, 407; 2/13; 324/263; 128/898

(56) References Cited

U.S. PATENT DOCUMENTS

| | | | | |
|---|---|---|---|---|
| 3,658,051 A | * | 4/1972 | MacLean ..................... | 324/263 |
| 4,134,395 A | * | 1/1979 | Davis .......................... | 600/407 |
| 5,092,835 A | * | 3/1992 | Schurig et al. ............... | 600/15 |
| 5,529,569 A | * | 6/1996 | Woo ............................ | 128/898 |
| 5,738,624 A | * | 4/1998 | Zablotsky et al. ............ | 600/15 |
| 5,782,743 A | * | 7/1998 | Russell ........................ | 600/15 |
| 5,827,170 A | * | 10/1998 | Gebran ........................ | 600/15 |
| 5,950,239 A | * | 9/1999 | Lopez .......................... | 2/113 |
| 6,048,302 A | * | 4/2000 | Markoll ........................ | 600/13 |
| 6,132,361 A | * | 10/2000 | Epstein et al. ................ | 600/13 |
| 6,379,295 B1 | * | 4/2002 | Woo ............................ | 128/898 |

FOREIGN PATENT DOCUMENTS

EP   0308700 A2 * 3/1989 ............ A61N/1/42

* cited by examiner

*Primary Examiner*—Eric F. Winakur
*Assistant Examiner*—Nikita R Veniaminov

(57) ABSTRACT

A method and apparatus for alleviating or curing human afflictions, ailments and diseases holistically by application of magnetism. A north pole surface of a magnet is applied to a portion of the neck, about 48 square inches, of a person being treated, and is maintained in contact for a time period or periods in accordance with total flux applied for the afflictions or ailments being treated. The magnet is maintained in contact for a time period or periods sufficient to elicit holistic effect of alleviation or cure and to detect ailments and cure in progress or a balanced treatment point. Magnet is being configured to accommodate the area being treated and having appropriate total flux.

28 Claims, 1 Drawing Sheet

TREATMENT OF AFFLICTIONS AILMENTS AND DISEASES

This invention is a result of a series of findings in my research for magnetic treatment since 1980 from which a method for holistic therapeutic effect of entire body by application of magnetism only to the hands or the head of patient was either already patented or is in pending by USA Patent Office under the tittle of Treatment of Ailments, Afflictions and Diseases and the respective Patent number is U.S. Pat. No. 5,529,569 Jun. 25, 1996 and patent application Ser. No. 09/570,510 Jul. 13, 2000 now U.S. Pat. No. 6,379,295 a continuation-in-part of application Ser. No. 08/939,429 Sep. 26, 1997 now abandoned.

BACK GROUND OF THE INVENTION

The present invention is directed to a method of applying magnetism only to the neck of patient for holistic effect of entire body. The conventional method is holistically effective and applicable to all ailments of human body for concurrent treatment utilizing meridians of Oriental medical theory and the brain control functions of self-survival healing mechanism. However, the neck application is uniquely effective with local pains of neck, throat, back, shoulder, upper extremity and related organs and parts along the respective meridian lines that run through the neck which include bladder, gall bladder, small intestine, triple warmer, large intestine, stomach, conception and governing vessel. The conventional method utilizes only hands and head of person and the present invention utilizes only neck of person or combined with head in magnetic application. When the neck application is utilized together with head magnetic application, effectiveness is increased with far less treatment time and faster healing, especially helpful in relief of pains associated with muscle tension and stiffness in the region of upper extremities, shoulder, neck, and cold allergy symptoms.

This is a method of pain relief and cure for holistic effect of entire body by applying negative magnetic flux, North pole, only to the neck portion of the body of the person treated, applying the principles of the Oriental Medicine utilizing the body's meridians known as pathway of life energy of the human body.

This method involves 2 unilateral and 6 bilateral meridians, and 5 unilateral acupoints and 14 bilateral acupoints that are being disposed through the entire neck, which are Governing Vessel of 3 acupoints, Conception Vessel of 2 acupoints, Bladder of 2 acupoints, Gall Bladder of 2 acupoints, Triple Warmer of 2 acupoints, Small Intestine of 3 acupoints, Large Intestine of 2 acupoints and Stomach of 3 acupoints whereas only hand and head meridians are being utilized in the referenced prior art.

This method is also extremely effective in relieving pain, inflammation and distress associated with chronic ailments related with the complicated energy systems of the meridians of the neck of the body. When magnetic fluxes are applied to the neck as shown in the diagram of FIGS. 2, 3 and 4 of drawings for therapeutical effect, life energy pathways of the neck meridians are directly affected. These important elements of the energy flow channels are being stimulated or restored instantly, upon application of magnetism to the neck, to elicit holistic therapeutical effect of entire body, thus breathing, circulation and energy flow are improved and order and balance of the energy system is restored to help body heals fast and relieves pains effectively, which are all observable and verifiable at sight.

This method enables body to sense responses from ill parts(location) and cure in progress in same way as the head and two-hand method of the referenced prior art, whereas note there is no response being occurred or detected from the healthy body with no ailments by application of magnetism. This phenomenon is believed to be some form of reaction of brain sick memory recall in response to the magnetic application and further to indicate that, when body is in sickness, pathway of life-energy (meridian) and sensory neurons of the nervous system are being hindered by some form of blockage and, when the flow is stimulated by magnetic flux, the flow hindrance causes responses and symptoms and, when the body is in health, the pathways are all clear and wide open for free flow thus causing no response or symptom even under magnetically stimulated condition in energy flow and neural transmission. An evidence to support this fact is that, when pain and ailment are cured by magnetic flux, all such responses and symptoms are gone and disappeared.

Magnets and magnetism have heretofore been utilized in the treating of human disease and afflictions. Any magnet configurated and sized to cover substantially the treatment area of the neck can be used for this method as long as it produces a sedative and healing effect in a range of $30\phi$ to $250,000\phi$ total flux and the north pole surface is flat and smooth for good contact to the neck. Total flux of up to $5,000\phi$ is believed to be ideal for pain control and management of sedative effect and total flux of above $5,000\phi$ is believed to be good for healing cure effect.

In comparison with the referenced method of prior art, this method of utilizing neck is more beneficial in some ways: more effective in relieving pains of related meridians such as organs of respiratory, circulatory and digestive systems covering neck, shoulder, back, arm, hand, nose, mouth, and easy of balanced treatment, etc.

Magnetic application in terms of alternative medicine or natural energy medicine has been widely recognized in the Western in recent years although this has been primarily an Oriental practice. Many innovative methods of magnetic treatment have been introduced, yet there is much left to be done for improvement.

Therefore, a general object of the present invention is to provide treatment for a wide variety of ailments and diseases for holistic effects, except for those requiring surgical treatment.

An object of the present invention is to provide such a method which utilizes magnetism applied to a portion of the neck of a person, thus to provide concurrent treatment of a plurality of ailments and afflictions of the entire body for holistic effect.

An object of the invention is to provide such treatment utilizing magnetism in simplified methods that can be practiced without specialized professional knowledge.

An object of the invention is to provide such methods that provide recovery from fatigue and which provide energetic, vigorous feelings.

An object of the invention is to provide such methods that provide substantial cures, relief of pain and rapid healing.

An object of the invention is to provide such methods that provide breathing control and/or improved circulation of the blood of the person to allow an optimum condition of the body systems, An object of the invention is to provide methods and techniques of treatment utilizing magnetism, independently of meridians or acupuncture points according to Oriental medicine.

An object of the invention is the provision of such a method which is economical and effective.

An object of the invention is the provision of such methods which, properly utilized, are safe and involve no harm to a patient and no adverse reaction or sequelae.

An object of the invention is the provision of such methods which involve the effecting of a balance of the energy systems of the body, in accordance with Oriental medicine theories, in treating ailments and applications.

SUMMARY OF THE INVENTION

The foregoing object and advantages, as well as others which will be apparent from the specification, are achieved by a method for treating and alleviating human afflictions, ailments and diseases by the application of magnetism to a person being treated.

A north pole surface of a magnet is applied to the person, only to a portion of the neck. Contact with magnet is maintained for a sufficient time period or periods to provide substantial alleviation or cure. The magnetic strength or total flux applied to the head may typically be from about 30φ to about 250,000φ total flux. The magnet may be maintained in contact with the person for a time period sufficient for the eliciting of substantial alleviation or cure. Magnet means are provided for application to the portion of the neck of a person being treated, with a north pole surface of the magnet means configurated to engage the portion or the area of the neck of the person.

BRIEF DESCRIPTION OF THE DRAWINGS

FIG. I is a perspective view showing a designated treating region utilized in the invention in the application of magnet means to the neck of a person.

DESCRIPTION OF THE PREFERRED EMBODIMENT

According to the present invention magnet or magnets are applied to the neck of the person being treated. The method of neck magnetic treatment involves application of magnetism by attaching a magnet directly to the designated treatment area of the neck only to elicit holistic therapeutical effect of the body.

In utilizing the method, where affliction or chronic ailment is treated, the neck is subjected to the magnetic treatment according to the invention.

Figure 1:
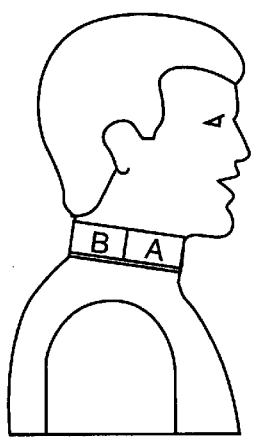

The method is an effective and powerful method of holistic treatment. The affliction, ailments and diseases of the entire body of a person may be treated concurrently by application of magnet means to the area of the neck of the person. In this method, magnets are applied directly to the designated area of the neck of a patient. A particular area of the neck where the meridians are disposed is being designated for holistic therapeutical effect and its size is about 72 square inches, 18 inches long and 4" inches wide, as shown in FIG. 1. The designated area of the neck covers all the way around its neck in about 4" wide. The governing vessel meridian is disposed through the median line of the head, neck and spinal column which is the intermediate line of the back part of the body, and the Conception meridian is disposed through the Adam's apple of the neck which is the intermediate line of the front part of the body, and bladder, gall bladder, triple warm, small intestine, large intestine and stomach meridian are disposed on both side of the median line of the neck. Thus, there are 2 unilateral meridians and 6 bilateral meridians, altogether 14 meridians, and 5 unilateral acupoints and 14 bilateral acupoints, altogether 33 acupoints, that are disposed in the designated area involving the neck method of holistic treatment. However, the 33 acupoints on the neck area are normally used by acupuncture technics to treat only the ailments associated with neck and throat, and they provides no means of holistic effects of entire body. But by applying magnetism to the area as a whole in accordance with the invention provides an effective means of holistic therapeutical effect of whole body.

In order to elicit such an holistic therapeutical effective and balanced treatment, the whole area of the round neck may be equally divided, as shown in FIG. 1, into 2 subregions such as front region "A" and back region "B" of the neck.

Figure 2:
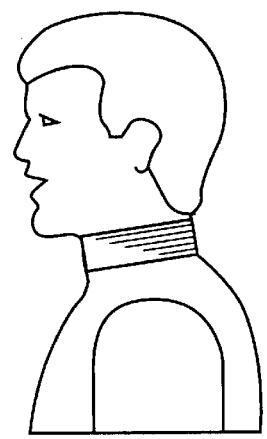
FIG. 2 is a perspective view showing the application of neck of a person to magnet means.
Figure 3:
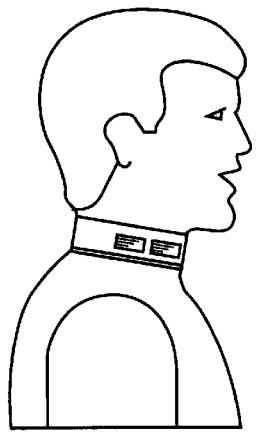
FIG. 3 is a perspective view showing the partial application of magnet means to a region of the neck of a person.
Figure 4:
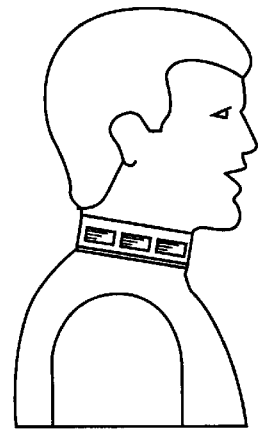
FIG. 4 is a perspective view showing the partial application of magnet means to all regions of the neck of a person concurrently.

All regions may be treated altogether as a whole, as shown in FIG. 2 of the neck, or partially by region at a time consecutively, as shown in FIG. 3, or partially by all regions together, as shown in FIG. 4. Thus, all meridians disposed through the neck are affected equally in balance and afflictions of all ailments related with the meridians and its organs of the entire body are treated concurrently and holistically.

This method of neck may be utilized with the head method together concurrently to increase effectiveness with less time of treatment which is extremely helpful especially in relieving pains of neck, back, shoulders and upper extremities, and cold allergy symptoms such as nasal congestion, nose running, cough and phlegm, etc.

The method of neck treatment by utilizing magnet or magnets are described as follows; Magnet or magnets are attached directly to the neck in the designated area, as shown in FIGS. 2, 3,4 and 5 of the drawings. The magnet or magnets may be applied evenly to the entire area of the neck concurrently with an equal total flux, as shown in FIG. 2 of the drawings, or partially by region at a time, as shown in FIG. 3 of the drawings, consecutively or concurrently, one by one with an equal total flux and an equal amount of treatment time, or partially by all regions together concurrently, as shown in FIG. 4 of the drawing, with an equal total flux and an equal amount of treatment time. In utilizing partial treatment by region at a time, or all regions together, balanced treatment should be practiced by using an equal total flux and an equal amount of treatment time.

Figure 5:
FIG. 5 is a perspective view showing a combined treatment of neck and head concurrently.
Figure 6:
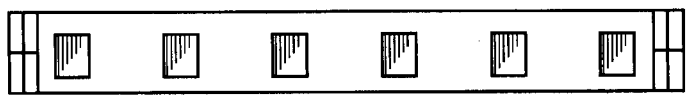
FIG. 6 is a perspective view showing a neck band utilized for a partial treatment of neck region concurrently.

Partial treatment may be practiced with any number of magnets sized more than 1/8" in diameter. Number of magnets used is determined by size and total flux of the magnet based on repelling and pulling power. When applying multiple magnets for partial treatment of all regions together, magnets are placed and spaced apart one another at an equal distance through out all regions of the neck, as shown in FIGS. 4 and 5 of the drawings, so that magnets are placed evenly around the entire neck in straight order.

Thus, all parts of the neck is treated equally of total flux for balanced treatment. When utilizing a combined method of the neck and head together, magnets should be applied to the entire area or partially of the all treating regions for both neck and head concurrently, as shown in FIG. 5, with same total flux and an equal amount of treatment time for a balanced treatment. In the case of using the combined method, all treating regions of the entire neck and head should be utilized concurrently for a balanced treatment effect. Applying magnets by region at a time is not appropriate in this combined method because too many meridians are involved with the neck and head that make difficult to achieve a balanced treatment.

In applying magnetism to the neck of a patient, the magnets are preferably configured and sized to cover partially or substantially the regional area of the neck, and preferably to cover substantially around the entire regions of the neck of the patient. Only the north pole of a magnet is applied.

In utilizing the area in the regions in application to the neck of a patient, it is typically and ordinarily necessary, in order to avoid a imbalance treatment in accordance with the Oriental medical theory, to apply magnet or magnets with an equal total flux for each and all treating area of the regions with an equal amount of treatment time for a balanced treatment. And, in addition, the balanced concept should also be applied by using the median line of the body which divided the neck into a half, left and right, and front and back, in order to avoid an imbalance condition of the body systems. Accordingly, when applying magnet or magnets around the neck, always place the magnets evenly at an equal distance, as shown in FIGS. 3 and 4 of the drawings, so that a balanced treatment is possible with an equal distribution of magnetic flux for each and all side of the neck, and this practice should be applied to all magnet sizes used under this neck method of magnetic application. Any magnet, permanent or electromagnet, may be utilized.

Typically, a flat magnet is employed, thus to provide well contact and substantially equal magnetic flux over the area of the neck.

In applying magnets to the neck of a patient, it is desirable that magnets of equal size and total flux are applied evenly to whole area of the neck and, in addition, for treatment partially by all regions of the neck together equal time of treatment should be practiced for a balanced treatment. The magnet may have any configuration appropriate to the area to which it is to be applied, such as square, rectangular, circular, oval, disc or bar. The size of the magnet should be such as to cover the entire regions of the neck or only the subregions of the neck or only a part of the subregions, at least more than $\frac{1}{8}$" inch diameter. Practically, any size appropriate for the neck is usable, however, the range of the magnet size preferred for this neck method is from $\frac{1}{8}$"×$\frac{1}{8}$" to 4"×18". Any magnet within this range of size can be effectively used.

In applying magnet means to the neck, magnet or magnets are attached to the neck skin in the designated area of the neck by using elastic band, neck-shaped wrapper or cover with Velcro fasteners for well contact, as shown in FIGS. 2, 3, 4, 5 and 6 of the drawings. Elastic band may include wraparound belts to securely hold the magnets sewn-in or encased in fabric lining, or adjustable Velcro type fasteners.

The magnet is positioned so that it is not readily removable or separable from the skin of the neck of the patient in order to be properly effective.

Magnets should be contacted well to the skin of the neck so that no gab between magnet and skin is allowed. As disclosed in the prior art of the head and two-hand method, the closer contact to the skin for magnet the better for effectiveness and, on the contrary, the farther from the skin the lesser effective.

The method is applicable for all afflictions, ailments and diseases associated with neck and its meridians. As stated, the method is extremely effective according to the invention, and serves to treat concurrently various or all afflictions and ailments of the entire body of a person. The method also serves to energize the person and relieve tiredness.

Effectiveness and applicability of the method are all observable at treatment site and easily verifiable instantly by patient during treatment in same way as prior art of head and two-hand magnetic method.

Treatment may begin with a relatively low power magnet, with successive application of magnets of increasing strength in accordance with the progress, response and feeling of the patient relative to relief. Typically, response is felt after 15 minutes, and within 30 minutes the patient can sense a cure in progress and a good feeling. Fifteen to ninety minutes of application is the optimum period for most effective treatment of most ailments or diseases.

The treatment time is typically 15 to 180 minutes, typically once or twice daily at interval of about 2–10 hours depending on total flux used and condition of the ailments or as often as needed whenever pain occurs.

The north side of the magnet is applied directly to the area of the neck and is left in place for 15 to 180 minutes. Pain is typically then gone.

Treatment commences upon application of the magnet and typically extends from 15 to 180 minutes, one or two times per day, at intervals of about 2–10 hours, or as often as needed whenever pain occurs.

At the end of each treatment, the magnet or magnets are removed. Most ailments or diseases are cured or greatly alleviated with one or two treatments. Treatment may be repeated until complete cure is effected. The treatment may be repeated at intervals in accordance with need and progress. For relatively serious or long-term ailments, treatment may extend for many days, and even for a few months or more. The effectiveness of treatment extends for about four to ten hours after removal of the magnet or magnets. Relatively simple or minor ailments or complaint is cured with one or two treatment.

The criterion used in this invention for therapeutic effectiveness and operativeness was "Did all pains of patient relieved concurrently from whole body within 15 minutes to two hour of each treatment session and did any side effect occurred or accompanied and did patient detect ailment and progress of cure and did patient feel energized".

Applying north pole of the magnet to the designated area of the neck of the patients, in accordance with the invention, relieves all pains related with the neck meridians of the body concurrently, regardless of cause and location, showing holistic total effect for whole body of the patient. Of various medical treatments, utilizing magnet means to the neck in accordance with the invention is found to be very effective to cope with pains and affliction. In practice of this holistic treatment, cause, location and names of ailments involved are not considered as important factors for treatment because all pains and afflictions associated with various ailments of whole body including chronic diseases are treated holistically and concurrently with excellent result of pain relief and cure, which are all observable and verifiable at site while treated within 15 minutes to three hours with no waiting time period for the treatment result, unlike conventional method. And in addition, patients can detect own ailments and cure in progress and final result as well by symptoms occurred in response to the magnetic application to the neck, and patients treated become energized and feel a power or strength in arms and wrists, especially when awaked in the morning.

Introduced below shows a typical example of the holistic total treatment for afflictions of all ailments of entire body for which the magnet device and the method were utilized—female patient, 66 years old, suffering from constant pain symptoms of neck, head, shoulder, back and arms for many years, was treated with this neck method by utilizing 6 magnets of 1"D×0,875T" with about 5,000ϕ total flux for one or two times every day. The pain symptoms were relieved holistically every time treated and the overall pain symptoms were substantially relieved with about one month treatment which is a remarkable result. The patient was able to live normal life in free of pain. Normally, it is impossible to cure or manage such symptoms in one month with the conventional method.

In proceeding according to the invention, the person or patient is preferably in a prone position or seated or any position comfortable for the application of magnetism. Magnet means may be applied to the neck while the person is in a standing, sitting, or recline position.

During the treatment, afflictions, ailments and diseases of a person are detected and sensed by the responses and symptoms of the person in response to the application of the magnetism in same way as prior art of two-hand or head magnetic method. The patient may sense responses involving complex symptoms, such as pain, strain, tightness, itch, warmth, coldness, etc. Such symptoms may be mixed and continue until the spot is cured or relieved. The cure in progress is sensed by the person during the application of magnetism in accordance with the invention.

The response or reaction of the patient to the neck treatment may involve the entire body. Symptoms occur from all diseased or afflicted areas of the body of the patient, and symptoms are usually continued until all ailments and diseases are greatly alleviated or cured. When all ailments are cured, all symptoms and responses are completely gone and this happens only when there is no ailment in the body. Thus there is no symptom or response occurring from healthy body even under magnetic application to the neck or head or hands. Such phenomenon is all observable and verifiable instantly by patient at treatment site while in treatment. As stated earlier, after application of the magnet for an appropriate time, the patient senses a response and therapeutical effect of cure in progress.

For internal illnesses or ailments or chronic diseases, after 15 minutes of application of the magnets to the neck, a response or reaction occurs in the patient, and the patient can sense a good response and active curing in 15 to 60 minutes of treatment. After approximately 90 minutes of application of the magnet, the response or reaction of the person's body gradually diminishes, the patient's body becomes relaxed, and a feeling of well-being permeates the patient's body.

This point in time of a treatment may be called as a balanced treatment point.

When balanced point is reached through the course of a treatment whole body becomes relaxed and then all pains and afflictions are gone with a feeling of well being.

At this very moment treatment should be stopped immediately—magnets should be removed from the neck skin, otherwise, the balance point may be reversed by over-treatment with a result of less effectiveness and a possible side effect.

Therefore, in accordance with the balance concept of Oriental medical theory, the point of being relaxed, easy state of human body occurring during a treatment is believed to be the exact point of a well balanced state of harmony in body systems in treatment. The magnet may typically be applied for 15 to 180 minutes and for not more than 180 minutes of a maximum balanced point, in order to prevent over-balanced treatment. Such balanced point in treatment is also dependent upon and is affected by factors including total flux, distance between magnet and skin, and condition of ailment and thereby each person might have a different balanced point.

However, in most cases, the balance points of treatment are within a range of 15 to 180 minutes. Therefore, the magnets may be applied within the specified time period needed to produce therapeutic effect and the following schedule may preferably be observed in the neck treatment:

Treatment: 15–180 minutes
Resting time: 2–10 hours
Frequency: 1–2 times daily/whenever pain occurs In application of magnetism to the neck of person, virtually all magnet, permanent and electromagnet, including weak magnets may be used and are all effective, whereas only relatively strong magnets with a total flux of more than 5000ϕ are utilized in the referenced prior art of two-hand method. Permanent magnets are preferred for economic reasons, but electromagnets can be utilized to advantage because their power can be varied or desired, within design limitations.

The range of total flux for magnets used is about 30ϕ–250,000ϕ and such total flux is measured at 0.001" from the north pole surface of the magnet means. The size of the magnet may typically be ⅛"×⅛" to 4"×18".

The effectiveness and curative results increase with increase of flux density(gauss) and total flux of the magnet applied to the person. The total flux applied to the patient is considered to be of key importance.

The following formula sets forth the relationship between total flux, flux density and magnet pole area:

$$\phi = BA$$

Where:
ϕ=total flux
B=flux density in gauss
A=area

Magnetic application to the neck has been found to be very safe, however, only for precaution, magnets should not be utilized in treating infants, pregnant women and person with heart pacemaker or metal implanted.

Thus there has been shown and described a novel treatment of afflictions and ailments with magnetism which fulfills all the objects and advantages sought therefore.

Many changes, modifications, variations and other uses and applications of the subject invention will, however, become apparent to those skilled in the art after considering this specification together with the accompanying drawings and claims.

All such changes, modifications, variations and other uses and applications which do not depart from the spirit and scope of the invention are deemed to be covered by the invention which is limited only by the claims which follow.

What is claimed is:

1. A method of treating and alleviating human afflictions, ailments and diseases holistically by application of magnetism to a plurality of treating regions of the neck of a person being treated, the method comprising the steps of:

providing magnet means having at least one north pole surface adapted for application to the plurality of treating regions of the neck;

designating at least two treating regions of the neck having a total size of about 72 square inches, covering about 4"×18" of a neck region all the way around the neck, said treating regions being divided into at least 2 subregions, according to shape of the neck; applying the north pole surface of the magnet means to at least one of the plurality of treating regions of the neck, the magnet having a size of ⅛"×⅛" to 4"×18" and shape appropriate to cover at least part of one of the treating regions of the neck; and maintaining the magnet means in contact with the at least one of the treating regions of the neck for a period of 15 to 180 minutes to heal and relieve afflictions, wherein the total flux of the magnetic means applied to the at least one of the treating regions of the neck is in the range from about 30φ–250,000φ1.

2. The method of claim 1, further including the step of repeating the application of the magnet means for at least one additional period of time.

3. The method of claim 1, further comprising repeating the time period for treatment at least once in a 24 hour period in an interval of about 2–10 hours in accordance with treatment progress.

4. The method of claim 1, further including:
applying the magnet means to a frontal region and a back region of the neck.

5. The method of claim 4, wherein applying the magnet means to the plurality of treating regions of the neck is performed in the order of the frontal region and the back region, or in reverse order.

6. The method of claim 1, wherein the applying step comprises first applying the magnet means to one of the treating regions of the neck of the person and then applying the magnet means to another of the treating regions of the neck of the person.

7. The method of claim 1, wherein the applying step includes applying the magnet means to multiple regions of the neck of a person concurrently.

8. The method of claim 1, wherein the applying step includes applying the magnet means to all treating regions of the neck of a person concurrently.

9. The method of claim 1, wherein the applying step includes applying the magnet means partially to multiple regions of the neck of a person concurrently.

10. The method of claim 1, wherein the applying step includes applying the magnet means partially to all treating regions of the neck of a person concurrently.

11. The method of claim 1, wherein a total flux of the magnet means applied to each one of the plurality of treating regions of the neck of the person is substantially equal.

12. The method of claim 1, wherein a total flux of the magnet means applied to each subregion of the plurality of treating regions of the neck is substantially equal.

13. The method of claim 1, further comprising applying multiple magnets to the treating region or regions concurrently by disposing the magnets evenly, spaced apart at an equal distance throughout a region or regions so that all parts of the treating regions of the neck of a person are treated equally with total magnetic flux for a balanced treatment.

14. The method of claim 1, further comprising placing a center of the magnet on a median line of the neck so that an intermediate line of the magnet is aligned with the median line of the body for equal distribution of magnetic flux for a balanced treatment.

15. The method of claim 1, further comprising applying additional magnets of substantially equal total flux to the treating regions of the neck of a person for a balanced treatment.

16. The method of claim 1, further comprising applying the magnet means consecutively or at intervals to selected treating regions of the neck of the person for equal time periods for a balanced treatment.

17. The method of claim 1, further comprising substantially covering the entire plurality of treating regions of the neck with the north pole surface of the magnet means.

18. The method of claim 1, further comprising substantially covering each of the plurality of treating regions of the neck with the north pole surface of the magnet means.

19. The method of claim 1, further comprising partially covering each of the treating regions of the neck with the north pole surface of the magnet means.

20. The method of claim 1, further including:
disposing retaining means for holding the magnet means to the neck to provide effective contact of the north pole surface of the magnet with the neck.

21. The method of claim 1, further including:
contacting the magnet means directly to the treating regions of the neck by using a band, wrapper or cover with magnets sewn-in or encased in any shape of form appropriate to fit the treating regions of the neck of a person.

22. The method of claim 21, wherein:
the band, wrapper or cover for contacting the magnet means to the treating regions of the neck of a person are made with any material that is safe to the neck and appropriate for fabrication.

23. The method of claim 1, further including:
utilizing the magnet means of the neck together with a second magnet means for treating a head of the person concurrently.

24. The method of claim 23, wherein the applying step includes applying the magnet means partially to at least one region of the treating regions of the neck and applying the second magnet means to all treating regions of the head of the person concurrently.

25. The method of claim 23, wherein the applying step includes applying the magnet means partially to all treating regions of the neck and applying the second magnet means to all treating regions of the head of the person concurrently.

26. The method of claim 23, wherein the applying step includes applying the magnet means to all treating regions of the neck and applying the second magnet means to all treating regions of the head concurrently.

27. The method of claim 23, wherein total flux of the magnet means and the second magnet means applied to each one of the plurality of treating regions of the neck and head of the person is substantially equal.

28. The method of claim 23, wherein a total flux of the magnet means and the second magnet means applied to each area of the plurality of treating regions of the neck and head of the person is substantially equal.

* * * * *